United States Patent [19]

Rowe et al.

[11] Patent Number: 5,612,050
[45] Date of Patent: Mar. 18, 1997

US005612050A

[54] APPARATUS AND METHOD FOR LOCAL APPLICATION OF POLYMERIC MATERIAL TO TISSUE

[75] Inventors: Stephen C. Rowe, Wellesley, Mass.; Jeffrey A. Hubbell, San Marino, Calif.; Stephen J. Herman, Andover, Mass.; Vae Sun, Palo Alto, Calif.; Michael F. Lang, North Andover, Mass.; George E. Selecman, Marblehead, Mass.; Frederick F. Ahari, Newton, Mass.

[73] Assignee: Focal, Inc., Lexington, Mass.

[21] Appl. No.: 476,124

[22] Filed: Jun. 7, 1995

Related U.S. Application Data

[63] Continuation-in-part of Ser. No. 36,128, Mar. 23, 1993, abandoned.

[51] Int. Cl.$^6$ ............................ A61F 2/02; A61M 1/30; A61K 31/74
[52] U.S. Cl. .................... 424/423; 424/78.08; 604/20
[58] Field of Search .......................... 604/20; 424/423, 424/78.08

[56] References Cited

U.S. PATENT DOCUMENTS

| | | |
|---|---|---|
| 2,170,599 | 8/1939 | Stricklen . |
| 2,518,486 | 8/1950 | Mende . |
| 3,238,941 | 3/1966 | Klein et al. . |
| 3,415,419 | 12/1968 | Jewett et al. . |
| 3,675,651 | 7/1972 | Meyer . |
| 3,707,146 | 12/1972 | Cook et al. . |
| 3,880,158 | 4/1975 | Gurney . |
| 3,987,000 | 10/1976 | Gleichenhagen et al. . |
| 4,080,969 | 3/1978 | Casey et al. . |
| 4,118,470 | 10/1978 | Casey et al. . |
| 4,346,108 | 8/1982 | Singer . |
| 4,385,344 | 5/1983 | Gonser . |
| 4,588,395 | 5/1986 | Lemelson . |
| 4,668,226 | 5/1987 | Omata et al. . |

(List continued on next page.)

FOREIGN PATENT DOCUMENTS

| | | |
|---|---|---|
| 0183372 | 6/1986 | European Pat. Off. . |
| WO90/01969 | 3/1990 | WIPO . |
| WO91/17731 | 11/1991 | WIPO . |
| WO92/21354 | 10/1992 | WIPO . |
| WO93/17669 | 9/1993 | WIPO . |
| WO93/16687 | 9/1993 | WIPO . |

OTHER PUBLICATIONS

Poppas, D.P. et al., "Chromophore Enhanced Laser Welding of Canine Ureters in Vitro Using A Human Protein Solder: A Preliminary Step for Laparoscopic Tissue Welding", The Journal of Urology, vol. 150, pp. 1052–1055, Sep., 1993.
Choma, T.J., M.D. et al., "$CO_2$ Laser Urethroplasty in the Rabbit: A Preclinical Model", Lasers in Surgery and Medicine, vol. 12, pp. 639–644, 1992.
Klioze, S.D. et al., "Development and Initial Application of a Real Time Thermal Control System for Laser Tissue Welding", The Journal of Urology, vol. 152, pp. 744–748, Aug. 1994.
Poppas, D.P. et al., "Laser Welding in Urethral Surgery: Improved Results with a Protein Solder", The Journal of Urology, vol. 139, pp. 415–417, Feb., 1988.
Poppas, D.P. et al., "Patch Graft Urethroplasty Using Dye Enhanced Laser Tissue Welding with a Human Protein Solder: A Preclinical Canine Model", The Journal of Urology, vol. 150, pp. 648–650, Aug. 1993.
Poppas, D.P. et al., "Preparation of Human Albumin Solder for Laser Tissue Welding", Lasers in Surgery and Medicine, vol. 13, pp. 577–580, 1993.

Primary Examiner—Carlos Azpuru
Attorney, Agent, or Firm—Wolf, Greenfield & Sacks, P.C.

[57] ABSTRACT

An apparatus is provided for applying to a surface of mammalian tissue including soft, living tissue an initially fluent material and then activating the material by exposure to an energy source. The material may be a liquid capable of polymerization to a non-fluent state by exposure to actinic light. The device, and methods that may be practiced in association with the device, enable a wide range of medical conditions to be treated including, for example, the application of a barrier to, soft tissue to prevent post-surgical adhesions.

33 Claims, 13 Drawing Sheets

U.S. PATENT DOCUMENTS

| | | |
|---|---|---|
| 4,702,917 | 10/1987 | Schindler . |
| 4,846,165 | 7/1989 | Hare et al. . |
| 4,878,492 | 11/1989 | Sinofsky et al. . |
| 4,911,926 | 3/1990 | Henry et al. . |
| 4,938,763 | 7/1990 | Dunn et al. . |
| 4,969,912 | 11/1990 | Kelman et al. . |
| 4,994,277 | 2/1991 | Higham et al. . |
| 5,009,655 | 4/1991 | Daignault, Jr. et al. . |
| 5,066,231 | 11/1991 | Oxman et al. . |
| 5,080,893 | 1/1992 | Goldberg et al. . |
| 5,092,841 | 3/1992 | Spears . |
| 5,100,429 | 3/1992 | Sinofsky et al. . |
| 5,126,141 | 6/1992 | Henry . |
| 5,147,203 | 9/1992 | Seidenberg . |
| 5,156,613 | 10/1992 | Sawyer . |
| 5,199,951 | 4/1993 | Spears . |
| 5,207,670 | 5/1993 | Sinofsky . |
| 5,209,776 | 5/1993 | Bass et al. . |
| 5,222,939 | 6/1993 | Tiefenbrun et al. . |
| 5,226,430 | 7/1993 | Spears et al. . |
| 5,292,362 | 3/1994 | Bass et al. . |
| 5,312,333 | 5/1994 | Churinetz et al. . |
| 5,324,519 | 6/1994 | Dunn et al. . |
| 5,334,191 | 8/1994 | Poppas et al. . |
| 5,372,585 | 12/1994 | Tiefenbrun et al. . |
| 5,410,016 | 4/1995 | Hubbell et al. . |

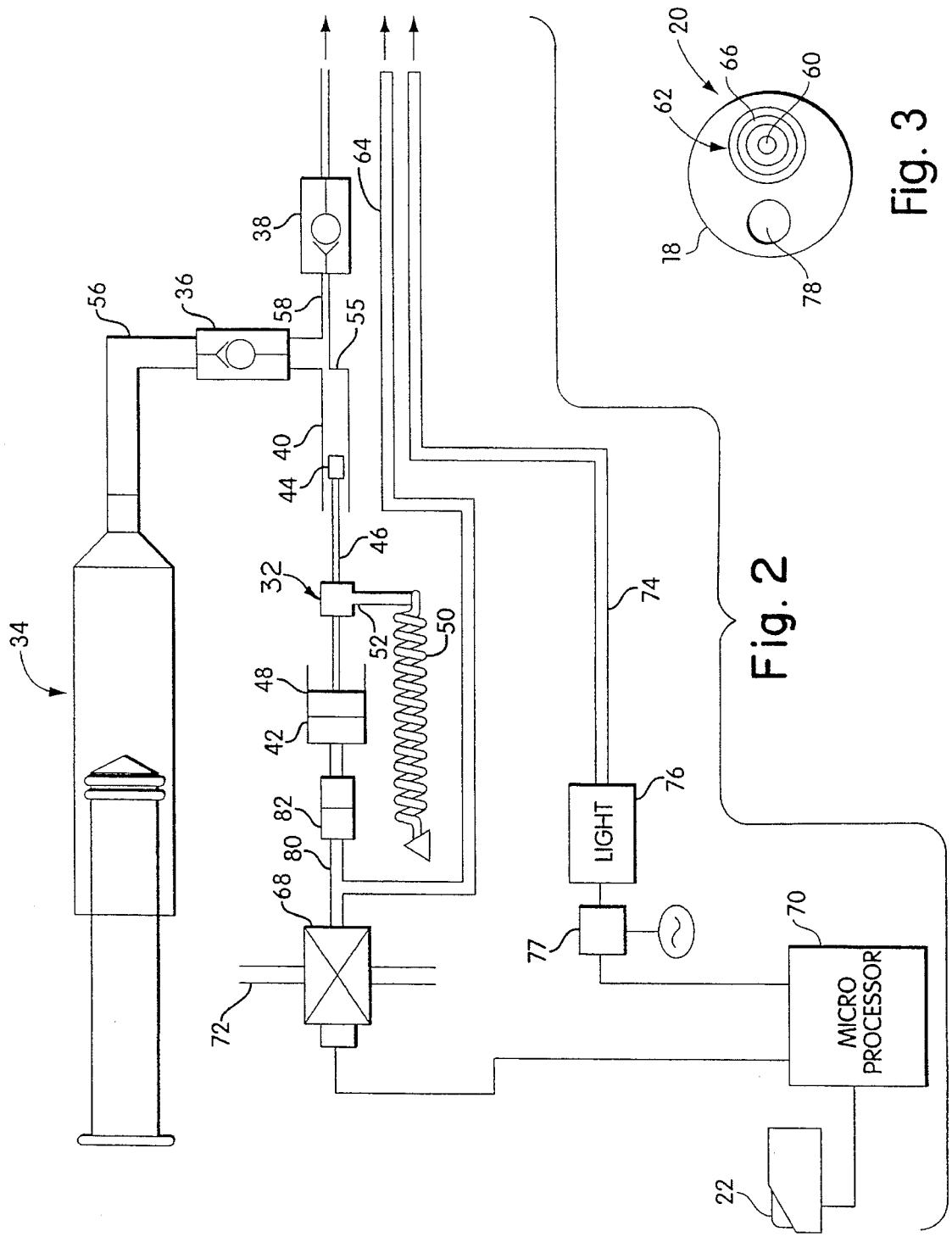

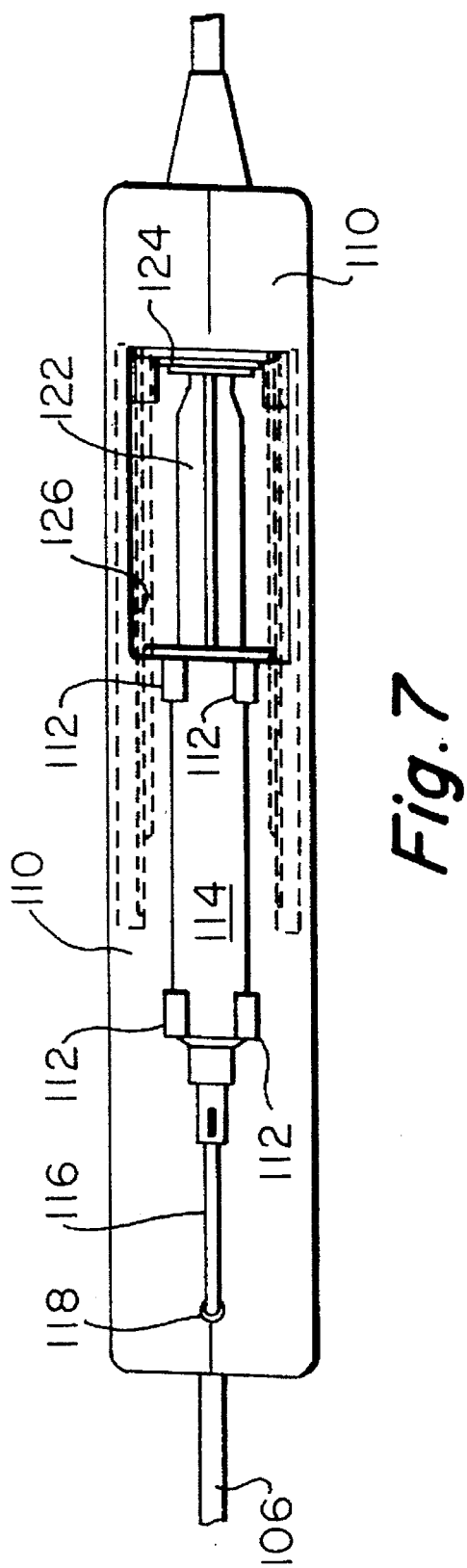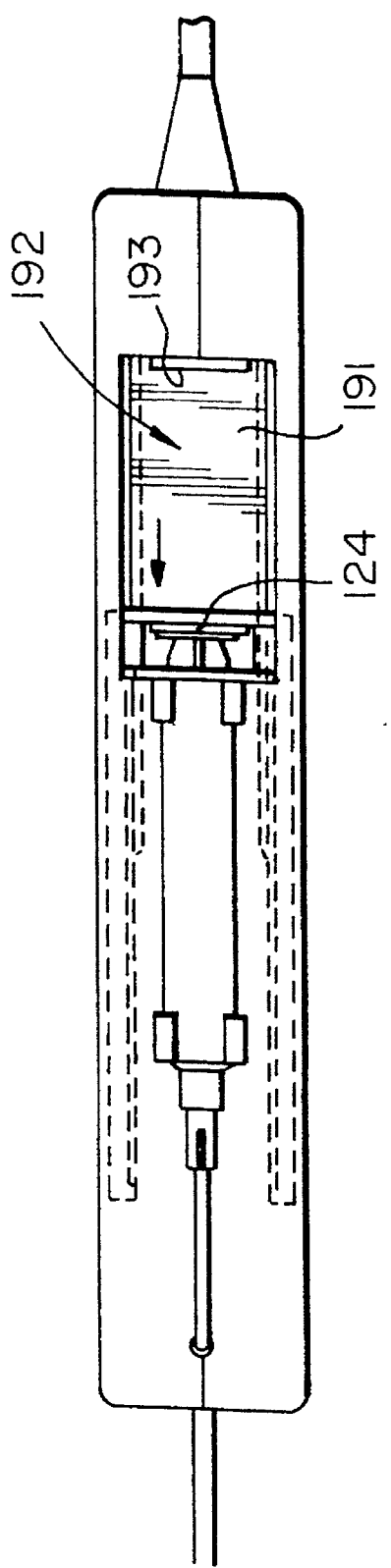

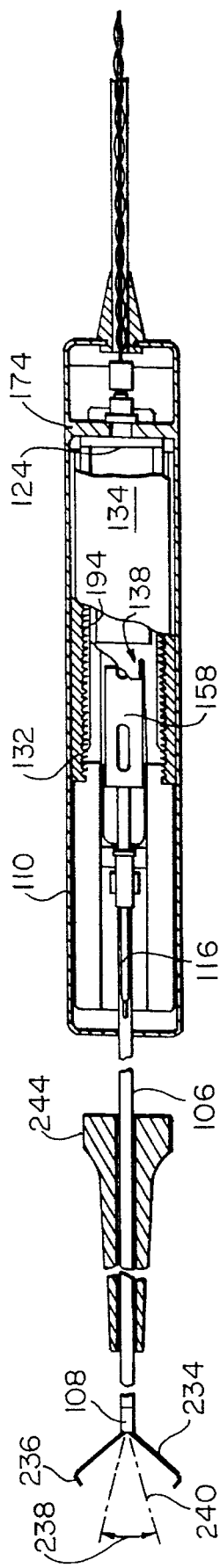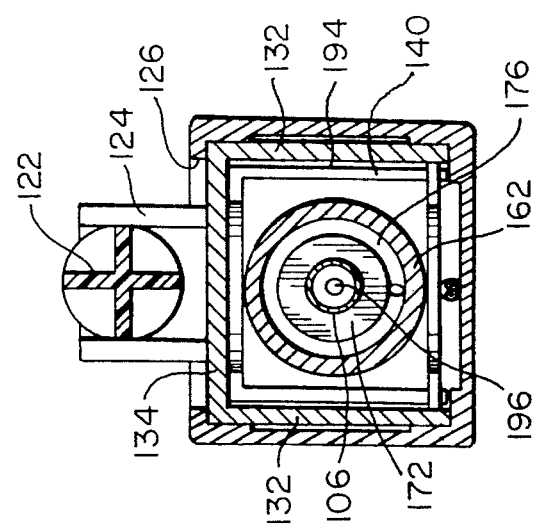
Fig. 8
Fig. 19

APPARATUS AND METHOD FOR LOCAL APPLICATION OF POLYMERIC MATERIAL TO TISSUE

This application is a continuation of application Ser. No. PCT/US94/03115, filed Mar. 23, 1994, which is a continuation-in-part of U.S. Ser. No. 08/036,128, filed Mar. 23, 1993, now abandoned.

FIELD OF THE INVENTION

This invention relates to devices and techniques for applying therapeutic polymeric material to living tissue.

BACKGROUND OF THE INVENTION

A number of photopolymerizable hydrogel polymers that may be applied to mammalian tissue, including soft, living tissue, in order to treat various medical conditions are disclosed in the following U.S. patent applications:

U.S. patent application Ser. No. 843,485 filed Feb. 28, 1992 (Hubbell et al.) and a continuation-in-part thereof, Ser. No. 08/022,687 filed Mar. 1, 1993, U.S. patent application Ser. No. 07/870,540 filed Feb. 28, 1992 (Hubbell et al.) and a continuation-in-part thereof, Ser. No. 08/024,657 filed Mar. 1, 1993.

The hydrogels disclosed in the foregoing applications may be applied to living tissue, for example, for the prevention of post-operative adhesions, the protection of tissue surfaces, the local application of biologically active species, and the controlled release of biologically active agents to achieve local and systemic effects. They also may be used as temporary or long-term tissue adhesives or as materials for filling voids in biological materials. The materials and conditions of application are selected to enhance desirable properties such as good tissue adherence without adverse tissue reaction, non-toxicity, good biocompatability, biodegradability when desired, and ease of application or handling.

The composition that will form the polymerized hydrogel may include a light sensitive polymerization initiator and is applied to the tissue surface in fluent form, as a liquid. The coated tissue then is exposed to light to polymerize the composition and render it non-fluent, in situ. The light is selected to be of an appropriate wavelength to efficiently initiate or sustain the polymerization and is of an appropriate intensity to achieve the polymerization within the desired time.

Reference is made to the above-identified patent applications for a detailed description of various hydrogels usable in this invention, their compositions, manufacture and general use. The disclosures of the above-identified applications are incorporated by reference as part of the disclosure herein.

SUMMARY OF THE INVENTION

The invention includes devices for applying a polymeric material to a surface of targeted tissue within a patient. The coating is applied as a predetermined volume of prepolymer composition which, after application, is irradiated with light to initiate and cause polymerization or gellation. The device includes a reservoir for the prepolymer liquid and an outlet adapted to eject the liquid onto the tissue surface in a predetermined pattern. A pumping arrangement is provided to cause transfer of a predetermined volume of prepolymer liquid stored in a reservoir to the outlet and for ejecting the liquid from the outlet. The outlet is arranged to cause the liquid to be emitted to form a predetermined pattern. The device also includes means for activating the fluent prepolymer liquid to render it non-fluent. The activating means may be a form of light that may be generated locally or conducted through an optical fiber from an external light source. The device has an optical emission aperture at its distal end and is arranged in association with the prepolymer outlet to direct light emission in the same direction. Operation of the various components of the system may be controlled by a microprocessor.

In one specific embodiment of the invention, the device is gas-powered and has an emission nozzle for the prepolymer liquid at its distal end. The nozzle arrangement is adapted to develop a low pressure emission of gas (e.g., $CO_2$) and a lumen is provided in the device and to communicate the gas to the nozzle from a source of pressurized gas. The outlet nozzle is arranged so that, while gas is being emitted, a bolus of prepolymer liquid injected into the gas stream will cause the liquid to form a desired pattern, as in a divergent spray. The device also includes an optical fiber having an emission aperture at the end of the device, adjacent to the outlet nozzle. After the prepolymer liquid has been applied to the tissue, the activating light is applied to render the liquid to a non-fluent state.

In another embodiment, the fluent prepolymer liquid is subjected to a sudden controlled pulse of high pressure to force a predetermined volume of the liquid through the delivery outlet. The arrangement includes a variable volume reservoir (e.g., a syringe) for the liquid that is operated rapidly and under a force adequate to develop sufficient pressure to emit the liquid from the outlet and deposit it on the tissue in a desired pattern. In this embodiment, the reservoir is mounted in a device that includes a driver element engageable with a movable part of the reservoir. The driver element is movable in predetermined increments to reduce the reservoir volume in sudden, controlled, forceful pulses to cause the ejection of the predetermined volume of liquid from the outlet. The device may include a spray nozzle at the outlet, with the driving system being sufficient to develop sufficient pressure, and pulse characteristics to cause the desired spray pattern. The device also may include an optical system to irradiate the applied liquid with light to activate the material.

The driving element may be powered by a self-contained power source such as a relatively high compression spring associated with a trigger mechanism that enables the spring first to be cocked (compressed) and then fired (released) to provide the driving force for the driver element.

In another aspect of the invention means are provided to facilitate positioning of the distal, emission end of the device with respect to the target tissue.

It is among the general objects of the invention to provide devices and techniques for efficiently and effectively applying a fluent polymerizable material (referred to as a "prepolymer") to targeted tissue, including living tissue, and for effecting polymerization of the fluent prepolymer composition in situ to a non-fluent state.

Another object of the invention is to provide a device of the type described in which the device applies a predetermined volume of the material for each operating cycle.

A further object of the invention is to apply the polymerizable material in a thin film sprayed on the targeted tissue.

An additional object of the invention is to provide means for determining the position of the distal end of the device from the tissue to be coated, and to facilitate aiming the device to control the thickness and location of the coating.

Another object of the invention is to provide a device of the type described that is suited particularly, although not exclusively, for use in endoscopic or laparoscopic surgery.

In another embodiment of the invention, means may be provided to facilitate the physician in determining the orientation and spacing of the distal end of the applicator device from the targeted tissue. Such means may take the form of a tissue engaging element attached to and extending distally a known distance from the distal end of the applicator. The physician can observe, as by a laparoscope, the contact of the distal end of the tissue contacting device thereby providing information as to the spacing and orientation of the applicator. In other aspects, the physician may obtain information as to the spacing and orientation of the device by directing light from the optical system against the targeted tissue and by observation of the light on the tissue to judge the distance and orientation of the distal end of the applicator with respect to that tissue.

In another aspect of the invention, means may be provided to aspirate, from the distal tip of the device, any excess drops of liquid that might collect on the tip.

BRIEF DESCRIPTION OF THE DRAWINGS

The foregoing and other objects and advantages of the invention will be appreciated more fully from the following further description thereof, with reference to the accompanying drawings wherein:

FIG. 2 is a schematic illustration of the operating elements of the applicator;

FIG. 3 is an end view of the distal end of the applicator shaft;

FIG. 7 is a top view of the housing of the embodiment of FIG. 6;

FIG. 8 is a fragmented, partly sectional illustration of the device as seen from above;

FIG. 19 is a sectional illustration taken along the line 19—19 of FIG. 6; and

FIG. 20 is a plan view of the top of the device after the syringe has been spent and in readiness for operation of the pawl release mechanism by which the driver is retracted to its rearward position.

DESCRIPTION OF THE PREFERRED EMBODIMENTS

The following detailed description of the invention is made in the context of use as an adjunct to laparoscopic surgery. It should be understood, however, that the invention may be used in other surgical environments where it may be beneficial to apply and polymerize material directly on tissue.

In the following description, the term "distal" or "forward" will refer to a direction toward the emission end of the devices (e.g., to the left in FIG. 6) and "rearward" or "proximal" will refer to the opposite end, that is, toward the physician.

Figure 1:
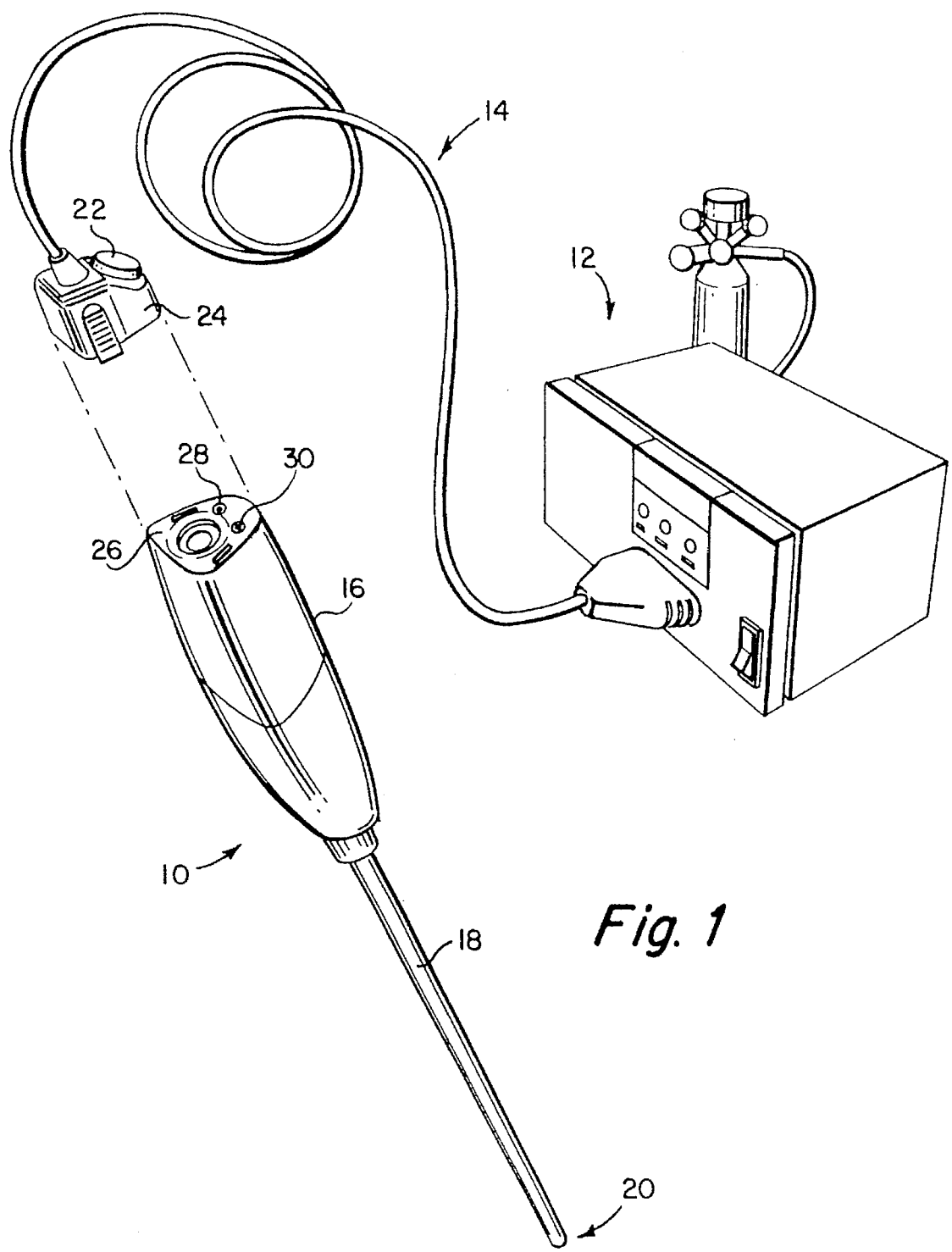
FIG. 1 is an illustration of the system including the applicator, the control module and the cable connecting the control module and applicator.

FIG. 1 is an illustration of the principal components of one embodiment of a system incorporating the invention. The system includes an applicator, indicated generally at 10; a control module, indicated generally at 12; and a transmission cord 14 that connects the control module 12 to the applicator 10. The control module 12 may include a light source, (not shown), such as those described in the above-mentioned Hubbell applications, to provide light necessary to initiate the polymerization reaction. The control module 12 also may include or be connected to a source of compressed gas such as ($CO_2$) and includes the valves and other devices adapted to facilitate control of the pumping system, described below. The control module 12 also may include microprocessors and associated electronics and displays to control and monitor operation and sequencing of the various elements of the system.

The applicator 10 includes a handle 16 and, in the illustrative embodiment adapted for use in a laparoscopic environment, a rigid shaft 18. The shaft 18 is attached to and extends distally from the handle 16. As will be described in further detail, the distal tip 20 of the shaft 18 includes an emission nozzle from which the prepolymer liquid is sprayed and an emission aperture of an optical path arranged to irradiate the sprayed tissue with light. The nozzle arrangement is adapted to develop a low pressure emission of gas and a lumen is provided in the device to communicate the gas to the nozzle from a pressurized source of the gas. The outlet is arranged so that while the gas is being emitted, a bolus of prepolymer liquid injected into the gas stream will be atomized to cause the liquid to form a desired pattern, such as a divergent spray.

The transmission cord 14, has a channel to communicate compressed gas to the applicator 10, an optical fiber or fiber bundle to couple light from the light source in the control module to the applicator 10 and electrical conductors to connect electrically the electronic controls in the control module with a triggering switch 22 associated with the applicator handle 16. The triggering switch 22 may be incorporated in an end cap 24 that is detachably connectable to the main portion of the handle 16. The proximal end of the handle 16, at the interface 26 with the end cap 24, includes connectors 28, 30 which, when the end cap 24 is attached are coupled with corresponding connectors in the end cap 24 to complete the optical and gas transmission paths from the end cap to the handle 16.

It is preferred that the components embodied in the handle 16 and shaft 18 be formed from low cost materials and components and that more expensive components be incorporated into the control module or the transmission cable and end cap. Thus, the handle and shaft portion of the device, or only the shaft portion, may be adaptable to disposable, one-time use.

FIG. 2 illustrates, schematically, an embodiment of the device that includes a gas-driven fluid pump arrangement, as well as the gas and light systems and their associated controls. The system includes a pump, indicated generally at 32, and a reservoir 34 that may be in the form of a syringe. In the illustrative embodiment, the pump mechanism 32 and syringe 34, as well as a pair of one-way valves 36, 38 and their associated conduits are contained with the handle 16. The pump 32 is pneumatically driven and includes a pump cylinder 40 and a drive cylinder 42. A piston 44 is slidably contained in the pump cylinder 40 and is connected by means, suggested schematically by rod 46, to a piston 48 slidably contained in the drive cylinder 42. The pistons 44, 48 are movable together in a pumping stroke (to the right in FIG. 2) or toward a retracted position in a filling stroke (to the left in FIG. 2). The pistons 44, 48 are biased toward a retracted configuration, as by a spring 50 illustrated. schematically as connected to the pistons 44, 48 through a bracket 52 secured to or part of the rod 46. Preferably, the device has a fixed stroke adapted to pump an identical volume of prepolymer liquid for each cycle. However, if desired, the length of the stroke of the pistons 44, 48 may be varied, as by providing an adjustable stop to vary the position to which the pistons are retracted. It is preferred that the pumping stroke extend from the retracted position to a position in which the piston 44 engages the end 55 of the pump cylinder 40. When the pump is retracted in a filling stroke, prepolymer liquid from the syringe 34 is drawn through a conduit 56 and the one-way valve 36 into the pump cylinder 40. When the pump is then driven in a pumping stroke, the liquid is ejected through line 58 and one-way valve 38 to and out of the central orifice 60 at the nozzle 62. The volume of ejected liquid is the same for each cycle of the pump.

The system also includes a pneumatic conduit 64 that extends through the handle 16 and shaft 18 and terminates at the nozzle 62. The nozzle 62 may be configured to include an annular outlet orifice 66 that surrounds the central orifice 60. Gas is communicated under pressure to the pneumatic conduit 64 through a normally closed solenoid valve 68. The solenoid valve 68 may be opened and closed under the control of a microprocessor 70. The valve 68 is in communication through line 72 with a source of compressed gas such as $CO_2$. The source of compressed gas can be any source with sufficient pressure such as a conventional tank and regulator, as in FIG. 1, or a small disposable gas cartridge mounted on the handle, or a reservoir on the handle or elsewhere, pressurized by mechanical means.

The applicator also includes an optical fiber 74 or a bundle of such fibers to transmit light from a light source 76 to a light emission aperture 78 at the distal tip of the shaft 18. The light source 76 is controlled by a switch 77 that, in turn, is controlled by the microprocessor. The light is switched on after the pumping stroke has been completed and is allowed to remain on for a predetermined length of time sufficient to assure full polymerization of the sprayed composition. The microprocessor and system controls may be configured to enable additional exposures of light independent of operation of the pump in the event that additional exposure is needed for full polymerization.

FIG. 3 illustrates the distal end face of the shaft 18 including the nozzle 62 and the distal emission face 78 of the optical fiber. The nozzle 62 and the distal emission face 78 may be arranged side-by-side and are oriented to emit a spray and light, respectively, along substantially parallel axes.

The nozzle, in the illustrative embodiment, is selected so that it will develop a divergent, generally conical spray that, preferably, will cover a spot of about 3 cm in diameter when the nozzle 62 is spaced about 2 cm from the surface of the target tissue. The optical fiber(s) is selected to have a numerical aperture such that the beam of light that is emitted from the emission aperture at the end of the fiber will diverge sufficiently to define an irradiated spot about 4 cm in diameter at a distance of about 2 cm from the distal tip 20 of the shaft 18. If desired, the emission aperture may be defined by a means other than the end of the fiber (e.g., a lens) to shape the beam of emitted energy or by a protective window. The preferred embodiment includes a configuration in which the spot defined by the irradiating light is greater than and includes the spot covered by the spray pattern when the nozzle 62 and light emission aperture 78 are spaced the same distance from the target tissue. This assures that when the applicator is maintained in the same position, the full area of tissue that has been sprayed will be irradiated sufficiently to effect adequate polymerization. It should be understood that other beam or spray patterns (e.g., rectangular, line, etc.) may be employed for use in special applications. It is preferred, however, that the pattern defined by the light be essentially the same as that of the spray in order to facilitate aiming of the device.

Figure 4:
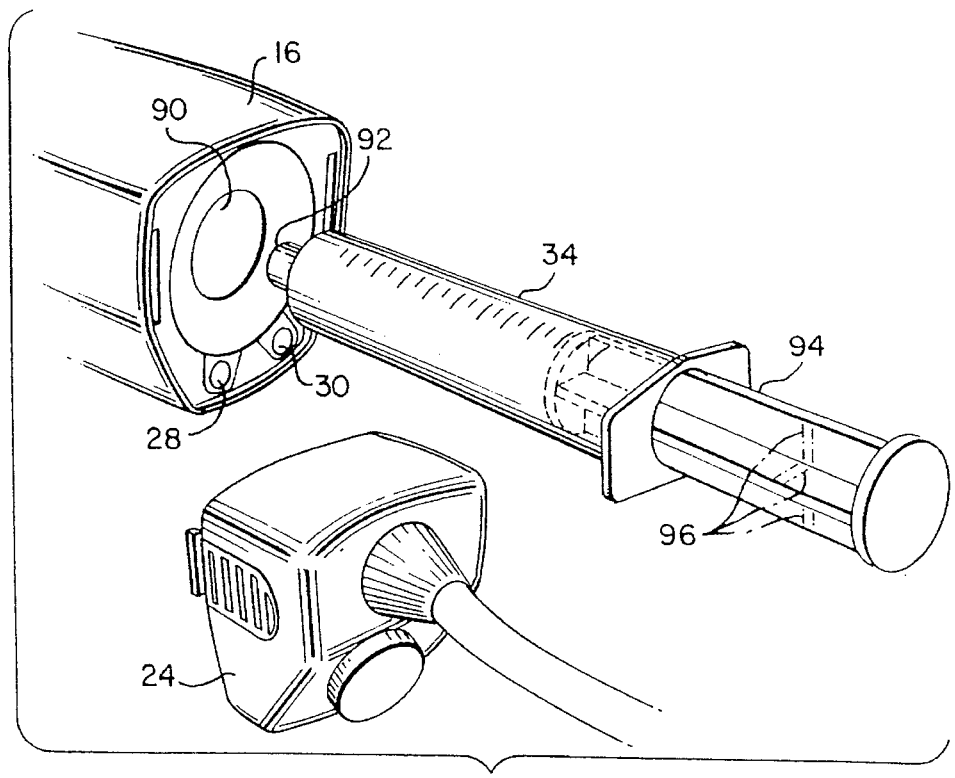
FIG. 4 is an illustration of the manner in which the syringe reservoir is loaded into the handle.

FIG. 4 illustrates a manner in which the syringe 34 may be received in the handle. The handle includes a socket 90 that is exposed when the end cap 24 is removed. The socket is receptive to the syringe and has, at the bottom of the socket, a fitting adapted to couple, in a sealed manner, to the distal tip 92 of the syringe. After the syringe has been loaded with prepolymer liquid, it is inserted into the socket to effect the coupling. The plunger 94 of the syringe then is advanced to eject prepolymer liquid into the conduits 56, 58 and through the check valves 36, 38, until the liquid drips out of the nozzle. The system then is primed. The plunger of the syringe may be provided with a weakened line 96 so that the proximate end of the plunger can be broken away after the device has been primed. With the proximal end of the plunger so trimmed, the end cap 24 then can be replaced on the handle 16 and the device is in readiness for use.

The prepolymer may be supplied in lyophilized form so that it may be mixed with suitable liquid (e.g., saline) immediately before being loaded into the syringe.

Figure 5:
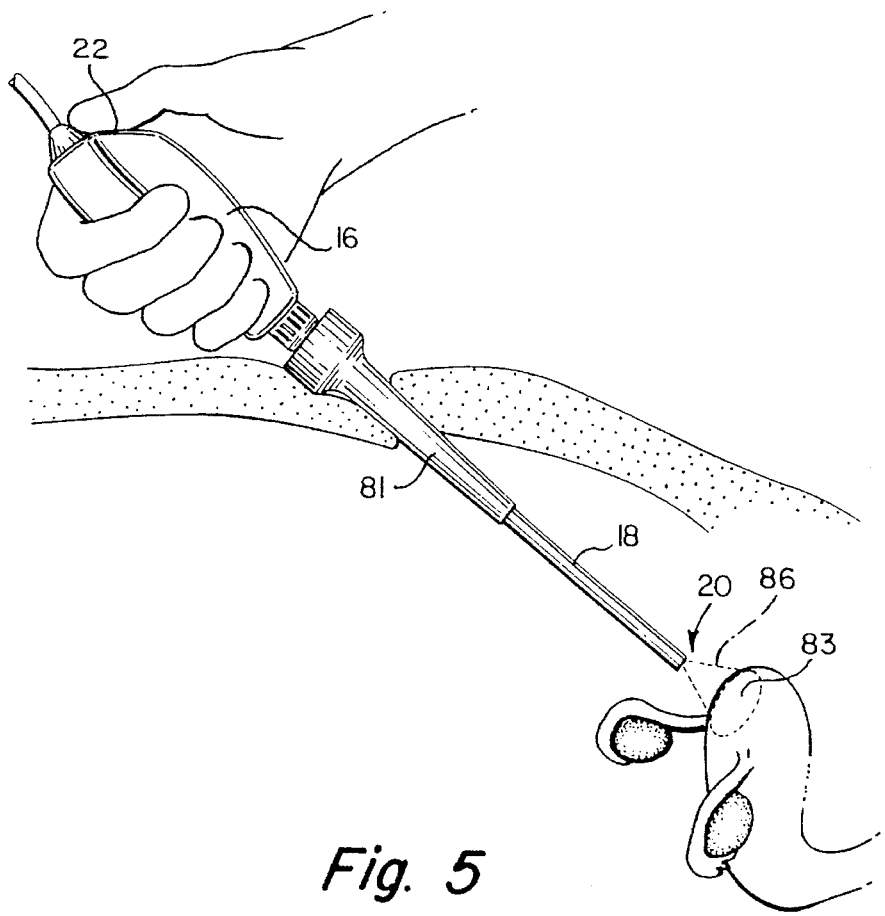
FIG. 5 is an illustration of the manner in which the device may be used in a laparoscopic procedure.

FIG. 5 illustrates the manner in which the applicator may be used in a laparoscopic procedure to apply a thin film (e.g., of the order of 200 microns thick per spray cycle) to a portion of the soft tissue comprising a patient's uterus. After the completion of the laparoscopic surgical operation here illustrated in connection with the uterus, and after removal of the surgical instrument from the trocar cannula, the applicator having been primed and set up in readiness for use, the shaft is passed through the trocar cannula 81. In the illustrative embodiment, the distal end 20 of the shaft 18 is positioned approximately 2 cm from the surface 83 of the uterus to be treated. The physician may observe the placement and orientation of the distal end 20 of the shaft through the laparoscope (not shown) that also is inserted into the patient through another trocar cannula (not shown). The device may be provided with supplemental means to facilitate aiming and positioning of the distal end of the shaft. For example, the device may include a control to operate the irradiating light source independently of the operation of the pump in order to preview the region at which the device is aimed. It will be appreciated by those skilled in the art that such aiming function including the timing and operation of the light independently of the other components of the system may be incorporated into the microprocessor or may be provided by a supplemental light source and/or control.

The device also may incorporate means to facilitate positioning of the nozzle a precise distance from the tissue to be coated. For example, a proximity and position detector indicator may tare the form of one or more slender, flexible feelers that project distally from the distal end of the device. When the distal tip(s) of the indicator engage(s) the tissue, that verifies the precise distance of the nip of the nozzle from that tissue. The physician can confirm, by observation through the laparoscope, that the feeler has contacted the tissue. In another mode, the physician may be assisted in determining the spacing and orientation of the distal end of the nozzle with respect to the target tissue by preliminarily irradiating the target tissue with light and observing the configuration of the light pattern on the tissue.

When the device is properly positioned and aimed, the physician actuates the system by triggering the switch 22. In this embodiment the microprocessor controls operation of valve 68 that serves to admit or shut off air to the system. The microprocessor is arranged to open the valve 68 to admit $CO_2$ from its source through conduit 72 and simultaneously to branch conduits 64 and 80. Line 64 directs gas to the annular outlet 66 on nozzle 62. The compressed $CO_2$ passes through a flow restrictor 82 and into the drive cylinder 42 to begin the pumping stroke. It will be appreciated that at the beginning of the pumping stroke the piston 44 will be fully retracted under the influence of the spring 50. The flow restrictor 82 serves to delay slightly the operation of the pump 32 sufficiently to enable the flow $CO_2$ out of the nozzle 62 to be fully established. Thereafter, as the prepolymer liquid is pumped out of the nozzle 62, it will merge with the gaseous stream to be formed into a divergent spray and directed against the tissue as suggested in phantom at 86 in FIG. 4. The spray will continue until the piston 44 has reached the end of its travel and abutment with stop 55. The gaseous stream emitted from the nozzle 62 is continued for a short time after the ejection of liquid has been completed. That assures that all of the emitted liquid will be converted into a spray and will be sprayed against the tissue surface. After the predetermined interval, which may be programmed into the microprocessor, the valve 68 is caused to shut off. The pump then is urged to its retracted configuration by the spring 50 to reload the pump cylinder 40 with a fresh charge of prepolymer liquid. After the prepolymer has been applied to the tissue surface, the light is transmitted through the optical fiber to polymerize the prepolymer.

It will be appreciated that where The area of tissue to be treated is greater than the area that can be covered and irradiated in a single cycle, the physician may apply a group of adjacent and overlapping spots to the tissue in order to cover fully the area to be treated.

FIGS. 6–17 illustrate another embodiment of the invention in which the mode of power for propelling the prepolymer solution includes a compression spring that is compressed and then released abruptly, the energy of the release being applied to a drive mechanism that advances forwardly the plunger of a syringe containing the prepolymer liquid. Means are provided for limiting the extent of travel of the plunger so that the sudden force applied by the release of the spring will cause a predetermined quantity of prepolymer liquid to be ejected through a nozzle, as in a spray, thereby coating the targeted tissue.

The applicator in this embodiment includes a housing 100 and a depending handle 102. The housing 100 may be formed from a pair of mirror image-half-sections secured together by fasteners 104 or other means. The device includes a tubular shaft 106 that may be rigid and formed from an appropriate biologically compatible material such as stainless steel. The shaft is adapted to be inserted into the patient, for example, as through a trocar cannula 81 as illustrated in FIG. 5. The shaft 106 may extend substantially fully through the length of the housing 100 and distally from the distal end of the housing. The shaft 106 includes a number of passageways, either in the form of separate internal tubes or defined by the lumen of the shaft, for communicating to the distal tip 108, liquid prepolymer and light for activation of the applied liquid prepolymer. The shaft also may include a passageway through which the region adjacent the liquid emission outlet can be aspirated to prevent liquid from dripping from the end of the tip 108.

Figure 6:
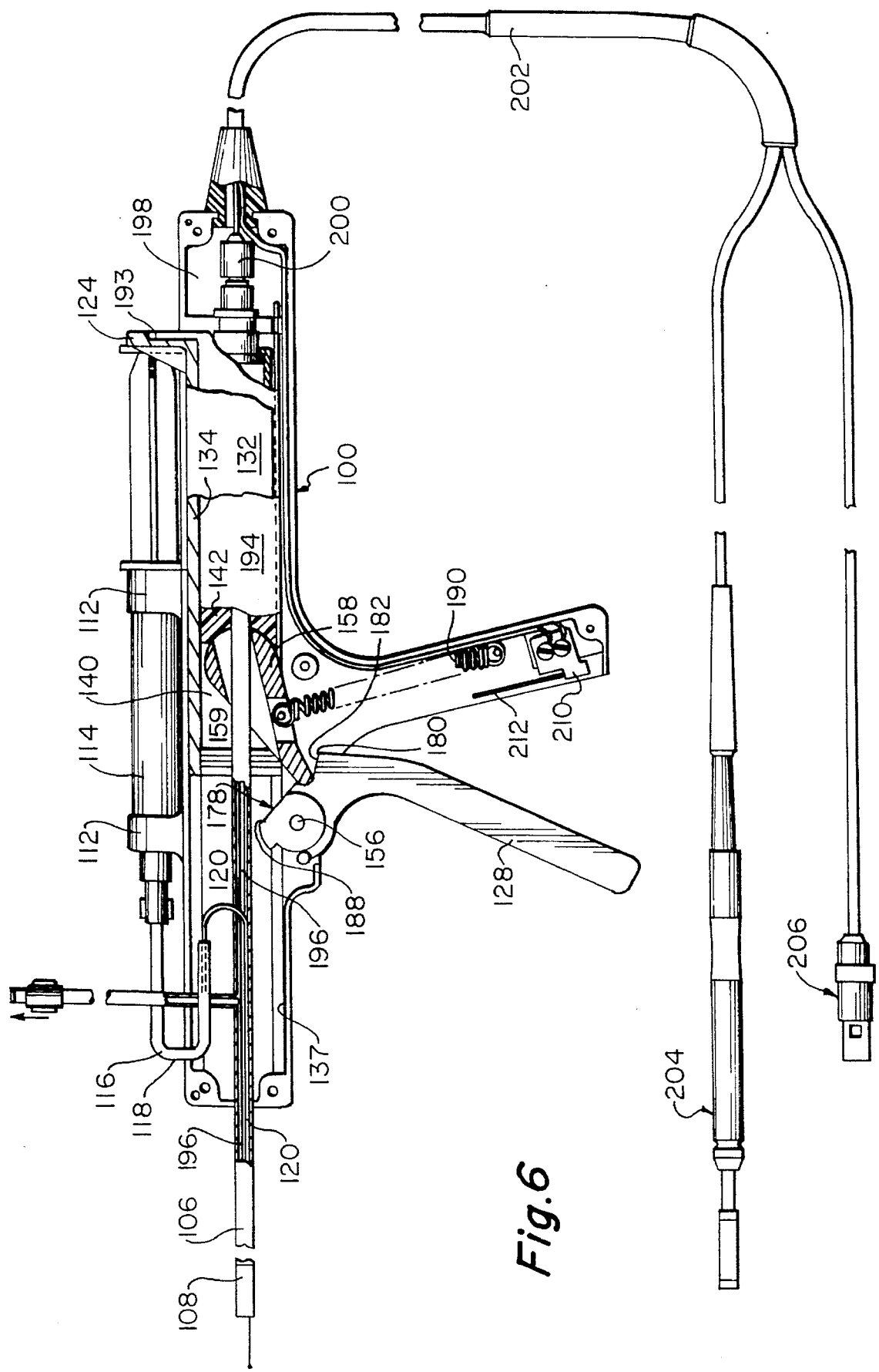
FIG. 6 is a fragmented sectional illustration of another embodiment of the invention.

The housing 100, when assembled, can be considered as including a top wall 110. The top wall is provided with brackets 112 arranged to securely, but detachably, hold a syringe 114. The syringe serves as a variable volume reservoir for the fluent prepolymer liquid. The outlet of the syringe is connected, as by a luer fitting, to a flexible conduit 116 that passes through an aperture 118 in the top wall 110. As shown in FIG. 6, the conduit 116 is connected to a liquid feed tube 120 within the housing. The feed tube 120 extends through the wall of the shaft 106 and through the shaft lumen to a nozzle arrangement at the distal tip of the shaft. The feed tube 120 may be formed from an appropriate material such as stainless steel tubing. The syringe 114 includes a plunger 122 that is operated in short, abrupt increments. The plunger is driven in a distal direction by a driver lug 124 that is movably mounted in the housing and projects upwardly through an opening 126 (FIG. 7) in the top wall 110, As described below in further detail, a driving mechanism contained in the housing 100, controlled by operation of a trigger 128, is operable to advance the driver lug 124 in short, abrupt and forceful increments.

The drive mechanism is illustrated in FIGS. 8–13. The mechanism includes a linear ratchet best illustrated in FIG. 11. The linear ratchet includes an elongated driver 130 having an inverted U-shaped transverse cross section and having downwardly depending sidewalls 132 and a connecting top wall 134. The lower edges of the driver sidewalls 132 are supported by and are slidable in a forward and rearward direction along a bottom wall 137 (FIG. 6) formed as part of the housing. The driver lug 124 is secured to and extends upwardly from the proximal end of the top wall 134 of the driver. The inwardly facing surfaces of the driver sidewalls 132 are provided with a plurality of teeth 136.

The driver 130 is driven forwardly by a linearly reciprocable driving pawl 138. The driving pawl 138 is disposed within the driver 130 and is slidable in a forward and rearward direction The driving pawl 138 is generally U-shaped, having a pair of forwardly extending arms 140 connected by a rear wall 142. The arms 140 are constructed to be flexible transversely and can bend inwardly toward each other. It may be desirable to provide a slot 144 adjacent the juncture of each arm 140 with the sidewall 142 to facilitate inward lateral bending of the arms 140.

Each of the arms 140 is spaced slightly from the inwardly facing teeth 136 on the driver sidewalls, for purposes described below. The distal end of each of the arms 140 is provided with several teeth 146 configured to engage the teeth 136 on the driver sidewalls 132. As will be described in further detail below, the teeth 136, 146 are arranged so that they lock together when the driving pawl 138 is advanced forwardly but can disengage, in ratchet-like fashion, when the driving pawl 138 is drawn rearwardly relative to the driver 130. Thus, it will be appreciated that as the driving pawl 138 is reciprocated forwardly and rearwardly within the housing (in a manner described below) the driver 130 will be driven forwardly in increments as the pawl 138 moves forwardly but can be held stationary (by means described below) while the driving pawl 138 moves rearwardly relative to the driver 130.

Figure 16A:
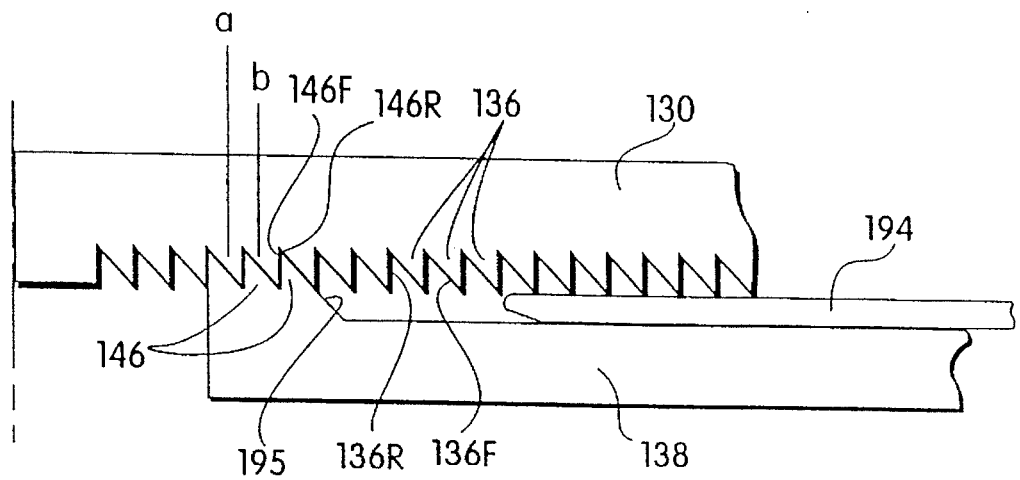
FIGS. 16A–16C illustrate sequentially the engagement of the driving pawl with the driver as the driving pawl is first retracted, re-engaged with a different group of teeth on the driver and then advanced one increment to advance the driver one increment in an ejection stroke.

The faces of the teeth 136, 146 that permit such linear ratcheting motion are shown in FIG. 16A. The teeth 136, 146 define a sawtooth configuration. The teeth 136 each have a rearwardly facing transverse face 136R and a forwardly facing inclined face 136F. The teeth 146 on the pawl 138 each include a forwardly facing transverse face 146F and a rearwardly facing inclined face 146R. The engagement of the faces 146F, 136R lock the driving pawl 138 to the driver 130 during forward movement of the driving pawl 138 while permitting the inclined faces 136F, 146R to slide with respect to each other as the pawl arms 140 flex resiliently inwardly until the teeth of the driving pawl engage the next rearwardmost teeth on the driver.

The driver 130 is maintained in its last advanced position during retraction of the driving pawl 138 by a locking pawl 148. As illustrated, the locking pawl 148 may comprise a thin U-shaped element having a pair of forwardly extending legs 150 joined at their rearward ends. The rearward end of the locking pawl 148 is secured to the housing 110 by any convenient means, such as a T-shaped element 150 received in a receptive bracket formed as part of the housing. The locking pawl 148 is disposed between the driving pawl 138 and the bottom wall 137 of the housing. The legs 150 of the locking pawl are flexible inwardly, similarly to the arms 140 of the driving pawl 138. The outwardly facing edge at the distal end of each of the arms 150 is provided with several teeth 154, identical in contour to the teeth 146 on the locking pawl 138. When the locking pawl 138 is driven forwardly to advance the driver 130, the engagement of the locking teeth 154 with the driver teeth 136 causes the arms 150 to flex inwardly to permit advancement of the locking pawl 138 and driver 130. When the locking pawl 138 is retracted, however, the engagement of the locking teeth 154 with the driver teeth 156 prevents rearward motion of the driver. This assures that when the locking pawl 138 is retracted, the driving lug 124 on the driver 130 will maintain a firm contact in the position against the proximal end of the syringe plunger, in readiness for the next ejection cycle.

FIGS. 6 and 9–12 illustrate, in further detail, the trigger and spring mechanism by which the device is actuated. The trigger 128 is pivotally mounted to the housing at pivot 156. The upper region of the trigger is engageable with the distal end of a compression link 158. The proximal end of the compression link is pivotally mounted to the driving pawl 138. between the arms 140, at pivot 160. The compression link is provided with a passageway 159 that receives a portion of the shaft 106. The passageway 159 is sufficiently wide so as not to interfere with the shaft during the full range of movement of the compression link 158.

The driving pawl 138 is limited in its range of forward and rearward movement and is biased continually toward the forward extremity of that range. The range of movement is limited by an arrangement that includes a tubular spring housing 162 attached to and extending rearwardly from the rear wall 142 of the driving pawl 138. The spring housing 162 may be attached to the wall 142 by a threaded connection 164. The rear end of the spring housing 162 is closed by an end wall 166. The end wall 166 is provided with an aperture 168 (See FIG. 13) that receives, slidably, a cylindrical rear mount 170. The forward portion of the rear mount 170 has a radially flared collar 172 that prevents separation of the spring housing 162 from the rear mount 170. Additionally, engagement of the flared collar 172 with the inner surface of the end wall 166 defines the forward limit of movement of the spring housing 162 and, therefore, the drive pawl 138. The rearwardly extending portion of the rear mount 170 is secured to a bracket 174 formed as part of the housing. In the illustrative example of this embodiment of the invention, the self-contained power source may be manually operated and may comprise a compression spring 176, that provides the power for ejection of the fluent prepolymer from the device, the spring 176 is contained within the spring housing 162 with its rear end in engagement, with the collar 172 of the end mount 170 and its forward end in engagement with a firm surface on the rear of the driving pawl 138. When the device is at rest, the spring 176 is compressed somewhat within the housing 162 so that the housing 162 and driving pawl 138 are in their most forward position, illustrated in solid in FIG. 13. As described below, when the device is cocked and in readiness to be fired, the housing 162 and driving pawl will be withdrawn a distance indicated at 169, to a position shown in phantom in FIG. 13.

Figure 10:
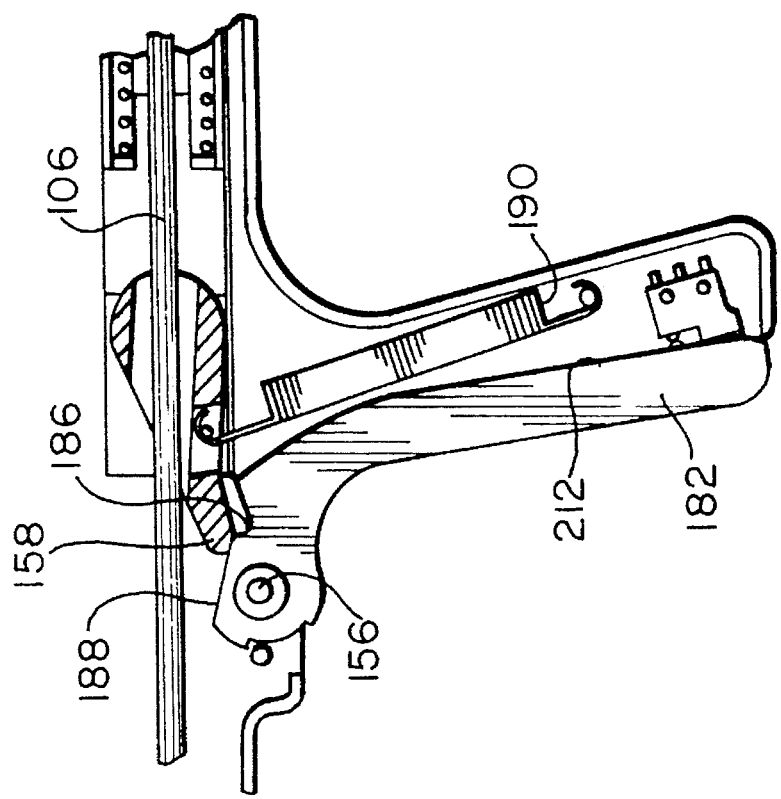
FIG. 10 is an illustration of the trigger mechanism in a fired configuration.
Figure 9:
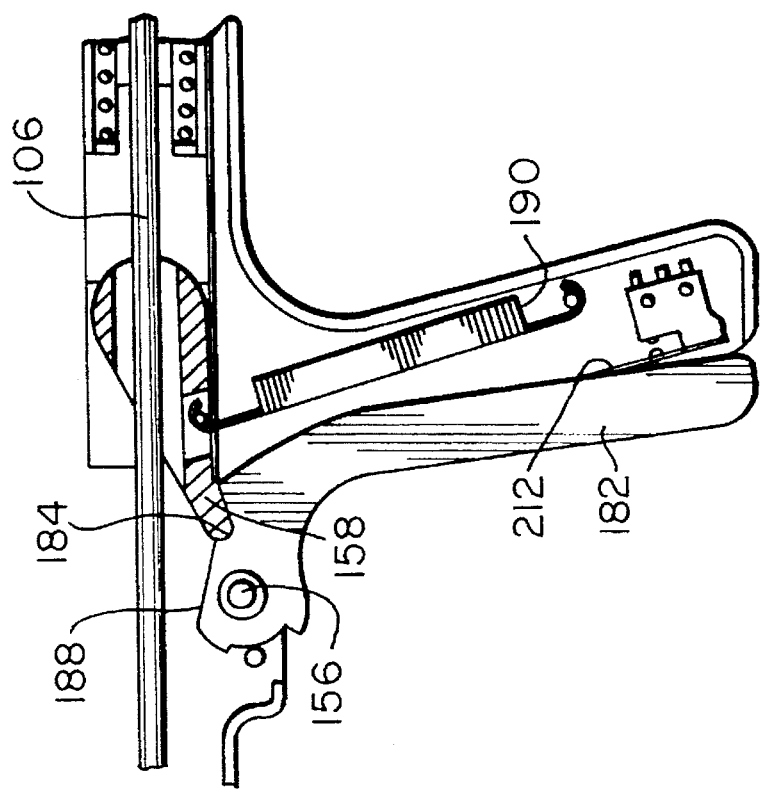
FIG. 9 is an illustration of the trigger mechanism in a cocked configuration.
Figure 11:
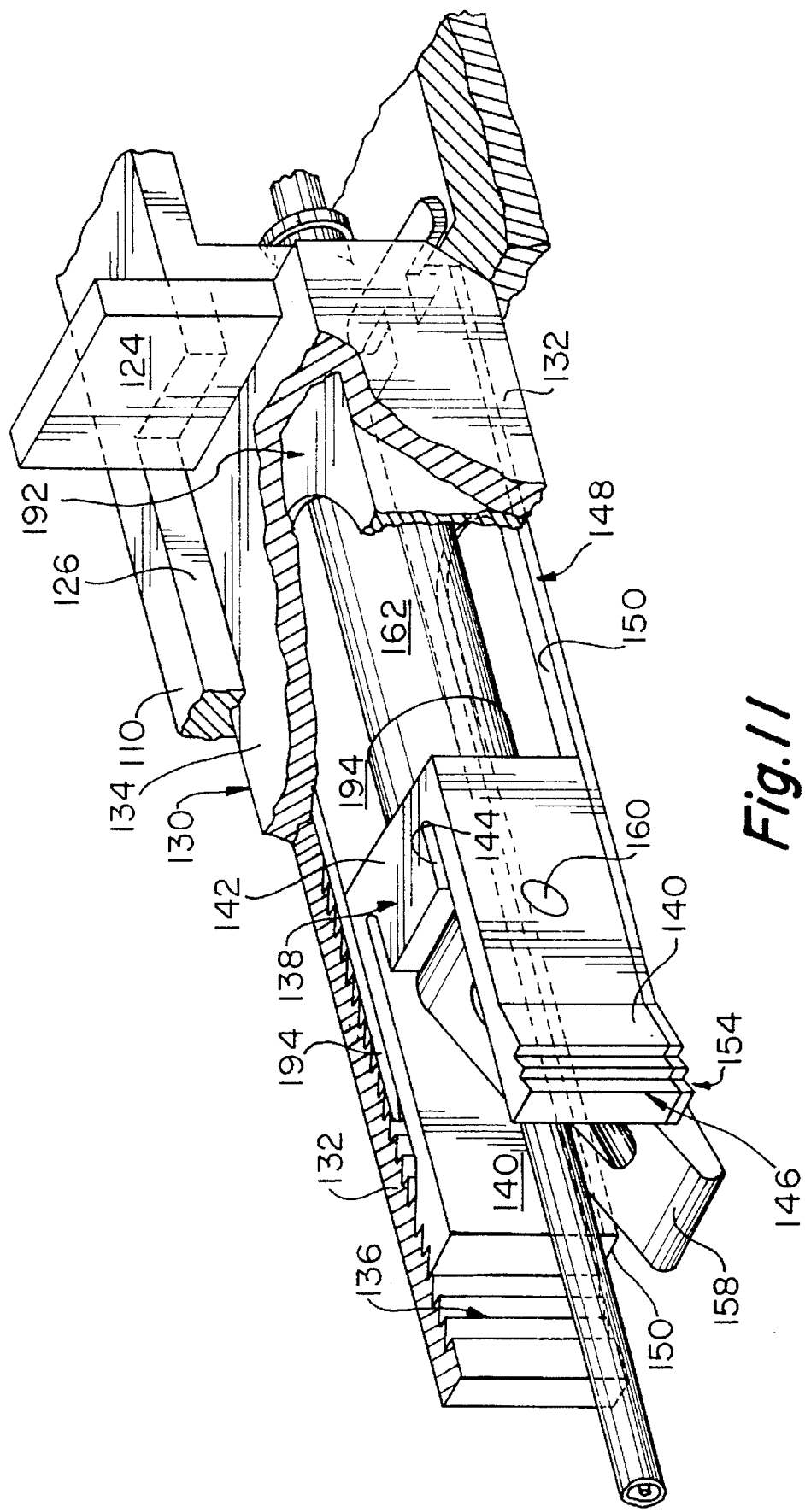
FIG. 11 is a fragmented perspective of a portion of the drive mechanism.
Figure 12:
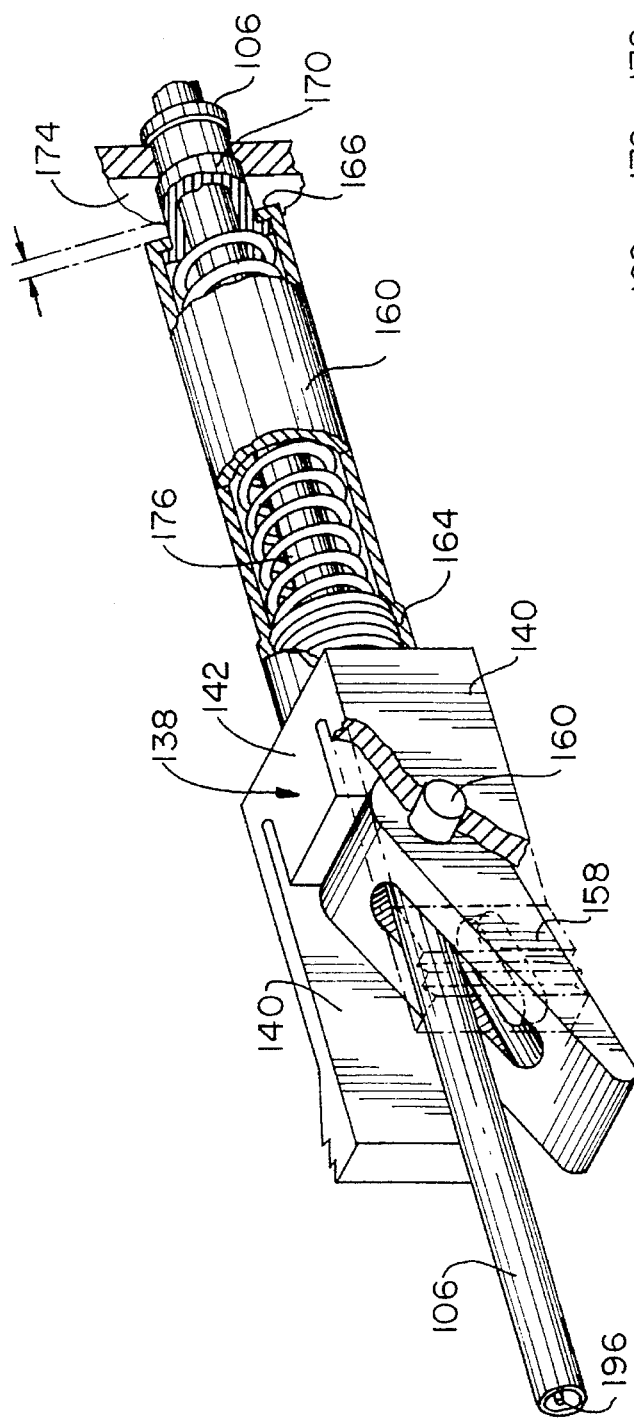
FIG. 12 is another fragmented illustration of a portion of the drive mechanism illustrating additional details thereof.

FIGS. 6, 9 and 10 illustrate the configuration of the trigger arrangement and its cooperation with the compression link in each of three positions including, respectively, a relaxed position (FIG. 6) in which the driving pawl 138 is in its forwardmost position, a cocked position (FIG. 9) in which the driving pawl has been urged rearwardly to compress the spring 176, and a released configuration (FIG. 10) in which the driving pawl has been released and driven forward by the spring and in which a light activation microswitch 210 has been operated to initiate the photopolymerization process. The trigger 128 is formed to include a contoured surface 178 at its upper end that defines a number of cam-like elements that engage and cooperate with the forward end of the compression link 158. In the illustrative embodiment, the contoured surface 178 may be considered as having a cam edge 180, first and second surfaces 182, 184 that mate to define a notch 186 (FIG. 10) and a third surface 186 that extends from the termination of the second surface 184. When the device is in its rest configuration (FIG. 6) the forward end of the compression link 158 is captured within the notch 186. A tension spring 188 is connected between the compression link and a portion of the handle 102 to continually bias the compression link downwardly (counterclockwise) as seen in FIG. 6. The force of the spring 188, through the compression link 158 maintains the trigger in its forwardmost position. A stop may be provided on the housing to limit the extent to which the trigger can pivot forwardly (clockwise).

The mechanism is operated by first squeezing the trigger to the cocked configuration (FIG. 9). In this configuration, the forward end of the compression link 158 remains nested in the notch 186 but bears directly against the second surface 184. in the cocked configuration, the cam edge 180 of the trigger is disposed against the underside of the distal end of the compression link 158. The linkage is arranged so that as the trigger is moved from the relaxed to the cocked positions, the pivot 160 and the driving pawl 138 are urged rearwardly a desired predetermined distance, such as the distance corresponding to the pitch between a pair of adjacent teeth 136. During the rearward cocking motion of the driving pawl 138, the driver 130 is maintained in position by engagement of the locking pawl 148. When cocked, the compression spring 176 is engaged and is in readiness to drive the driving pawl 138 and the driver 130 forwardly, thereby advancing the plunger of the syringe.

The device is fired by further squeezing of the trigger which causes the cam edge 180 to urge the forward end of the compression link upwardly over the second surface 184 and onto the third surface 188. The third surface 188 is oriented so that when the trigger is in the fired position, the distal end of the compression link is free to slide forwardly over the third surface. That permits the energy that had been stored in the compression spring 176 during the cocking step to be released abruptly to drive the driving pawl 138 and driver 130 forwardly. The forward movement is limited by engagement of the end wall 166 of the spring housing 162 with the radial collar 172 on the rear mount 170.

Figure 13:
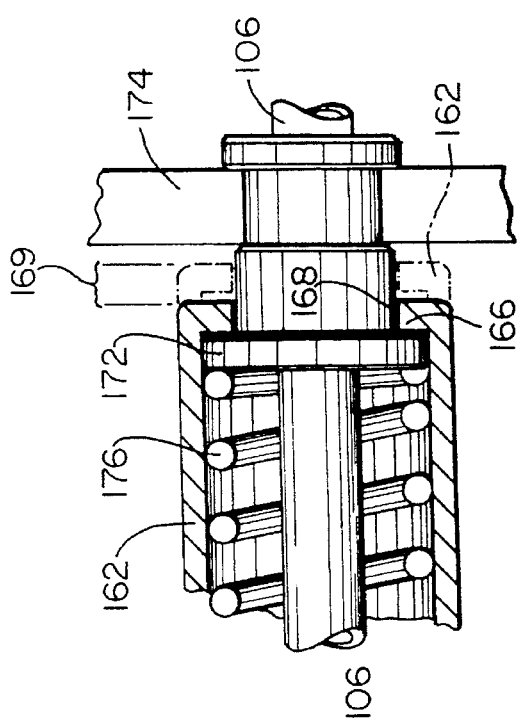
FIG. 13 is an enlarged sectional illustration of the means for limiting the extent of movement of the driving pawl.
Figure 16B:
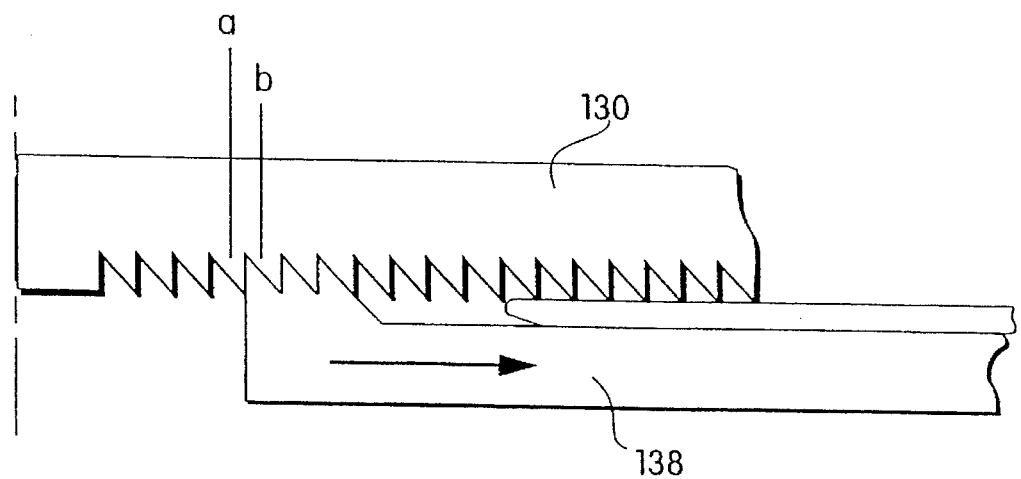
Figure 16C:
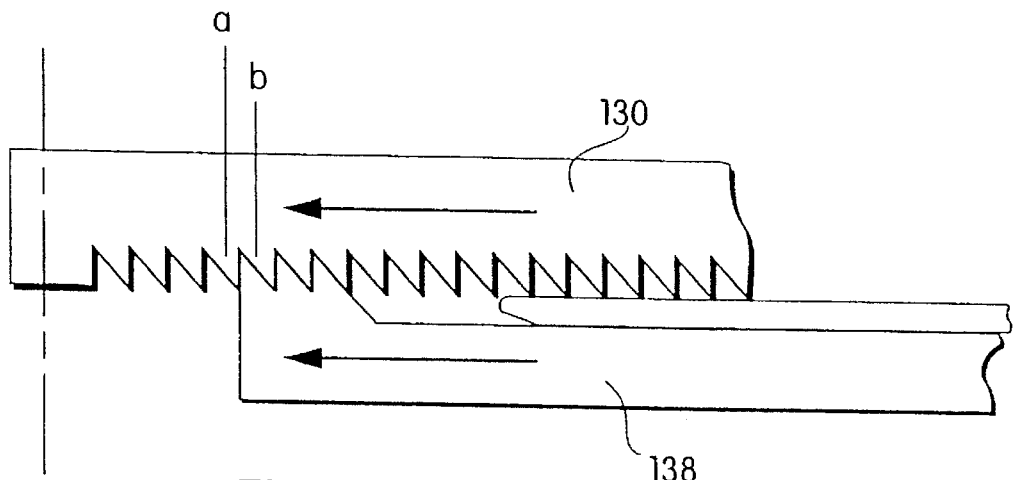
Figure 17A:
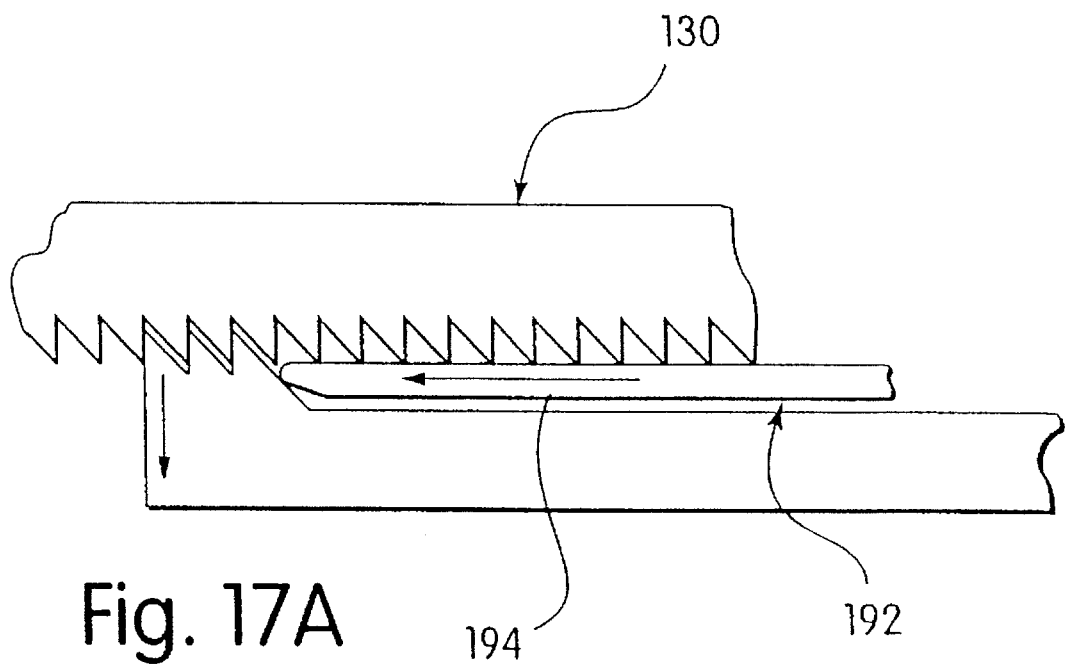
FIGS. 17A–17B illustrate the manner in which the pawl release effects disengagement of the driving pawl from the driver.
Figure 17B:
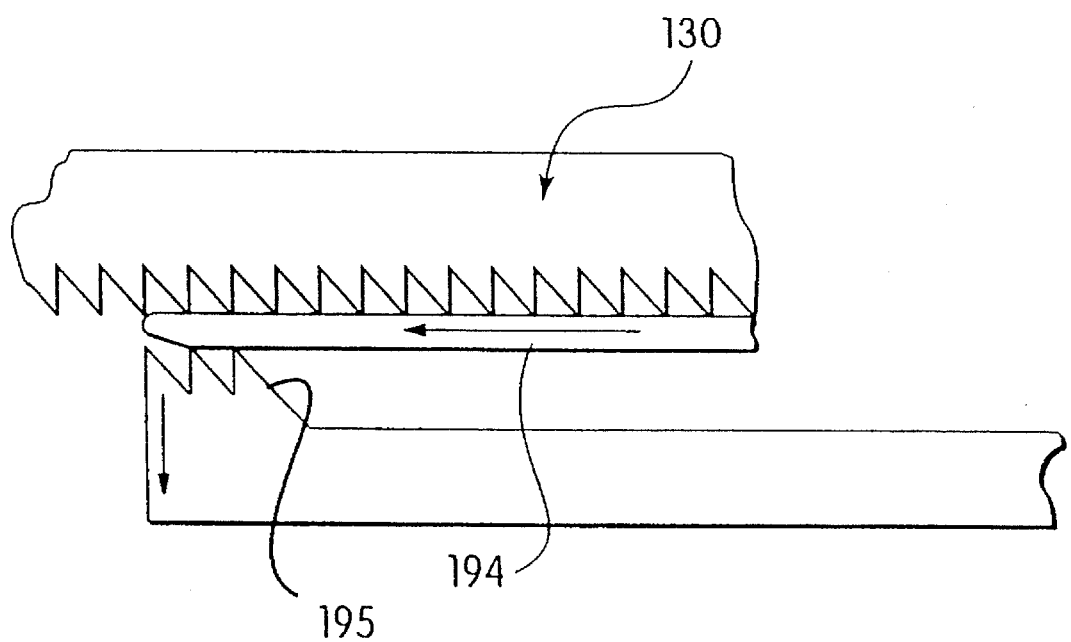
Figure 18:
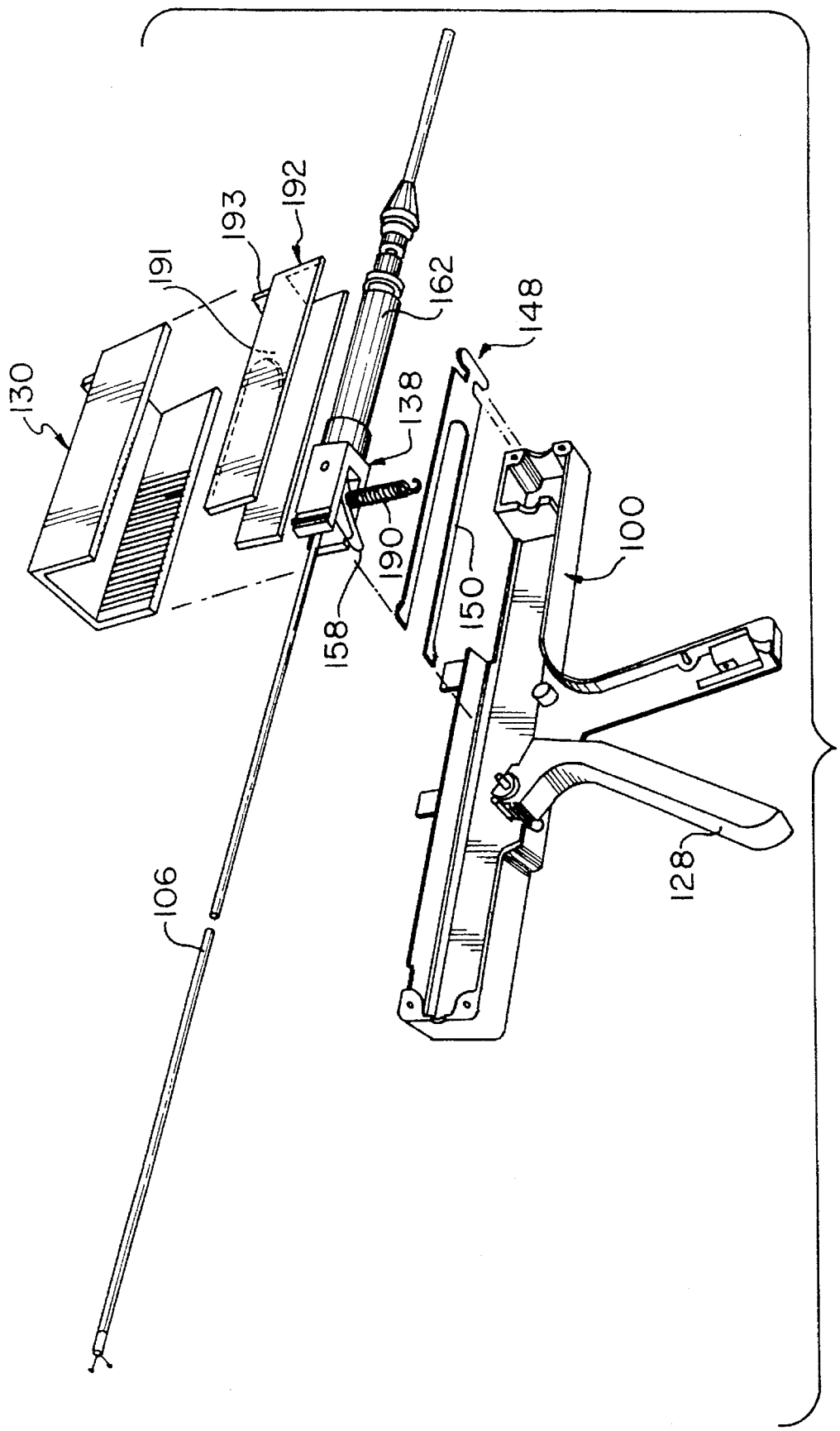
FIG. 18 is an exploded view of the components of the device.

FIGS. 16A–16C illustrate in enlarged diagrammatic detail the movement of the driving pawl and driver. FIG. 16A illustrates the driving pawl in engagement with several teeth, including those designated a and b of the driver 130 with the device at rest. When the driving pawl 138 is withdrawn rearwardly during cocking, it moves rearwardly a distance equal to the pitch of a pair of adjacent teeth as shown, but less than two pitches. In this configuration, the compression spring 176 will have been further compressed in readiness to drive the driving pawl forward. FIG. 16C illustrates the device after it has been fired, with the driving pawl 138 having advanced the driver 130 an increment corresponding to the pitch between a pair of adjacent teeth and The distance 169 (FIG. 13). Release of the trigger 128 by the physician allows clockwise rotation of the trigger 128 and allows the compression link 158 to rotate counterclockwise until its distal end can fall from the third surface 188 to the first surface, resetting the mechanism in prepartion for another firing sequence. The device is then ready for the next cocking and firing sequence.

After the device has been operated repeatedly to deplete the prepolymer liquid in the-syringe, the syringe must be replaced. That requires that the driver be retracted rearwardly so that it can receive the freshly loaded syringe with a fully extended plunger. Retraction of the driver 130 requires that the driving pawl 130 and locking pawl 138 be disengaged from the teeth 136 of the driver 130. To that end, the device includes a pawl release, indicated generally at 192. The pawl release 192 is in the form of a generally inverted U-shaped member nested within the driver 130 and slidable longitudinally of the device. The pawl release 192 includes a top wall 191, an upwardly extending tab 193 at its rear end and a pair of laterally spaced forwardly extending release arms 194 that fit and are movable between the arms 140 of the locking pawl 138 and the teeth 136 on the driver sidewalls 132. The distal end of each of the arms 140, in the region of the teeth 146, is thicker than the more proximal portions of the arms 140 and is formed to define an inclined wedge surface 195. Identically contoured wedge surface 197 is formed adjacent the teeth 154 on the locking pawl 148. When the pawl release 192 is advanced forwardly, the forward ends of its arms 194 engage the wedging surfaces 195, 197 to disengage them from the teeth 136 on the driver 130. The driver 130 and pawl release 192 then can be withdrawn rearwardly in unison, the arms 194 of the pawl release maintaining the teeth on the pawls 138, 148 out of engagement with The teeth 136 and the driver. When the driver 130 and the pawl release 192 have been retracted to the point that the ends of the arms 194 are withdrawn from between the teeth on the pawls and the driver, the teeth 136, 146 and 154 reengage. The device then is in readiness for reloading with a fresh syringe.

The optical system for the device includes an optical fiber assembly, indicated generally at 196 that includes an optical fiber, preferably contained within a protective housing, such as an elongated helical coil (not shown). The optical fiber extends fully to the proximal end of the shaft 106, where the shaft passes through the rear mount 170. The housing 100 may be formed to include a proximal chamber that contains transition fittings 200 by which the optical fiber is transitioned from its emergence from the proximal end of the shaft 106 to its entrance into cable 202. The cable includes a bifurcation at its proximal end. One end of the bifurcation comprises an optical connector 204 to connect the optical fiber to an appropriate source of activation light. The other bifurcation includes an electrical connector 206. The electrical connector 206 is connected to wires 208 that lead back into the housing 100 into a microswitch 210 in the handle. The microswitch 210 includes an actuator 212, positioned to be actuated by the trigger 128 when the trigger has been pulled to the fire position (FIG. 10). The electrical connector 206 is connected to the light source such that actuation of the microswitch 210 will cause the light to be turned on to irradiate the deposited prepolymer and cause it to polymerize to a non-fluent state.

Figure 14A:
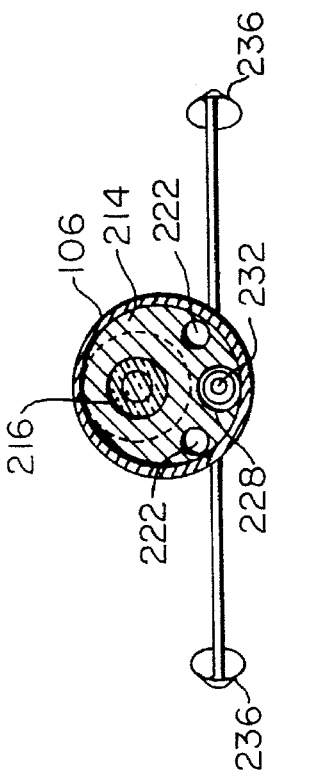
FIG. 14 is an end view of the distal tip of the device shown in FIG. 6.
Figure 14:
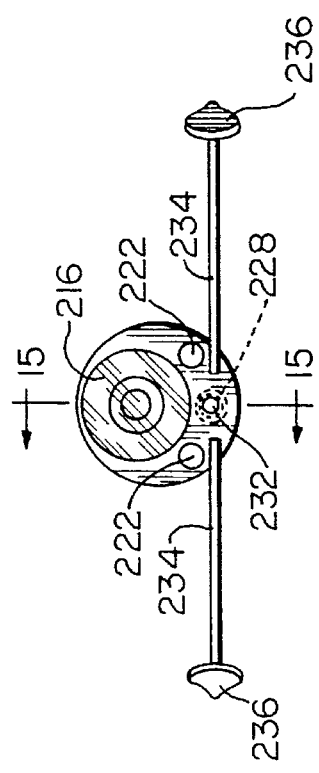
Figure 15:
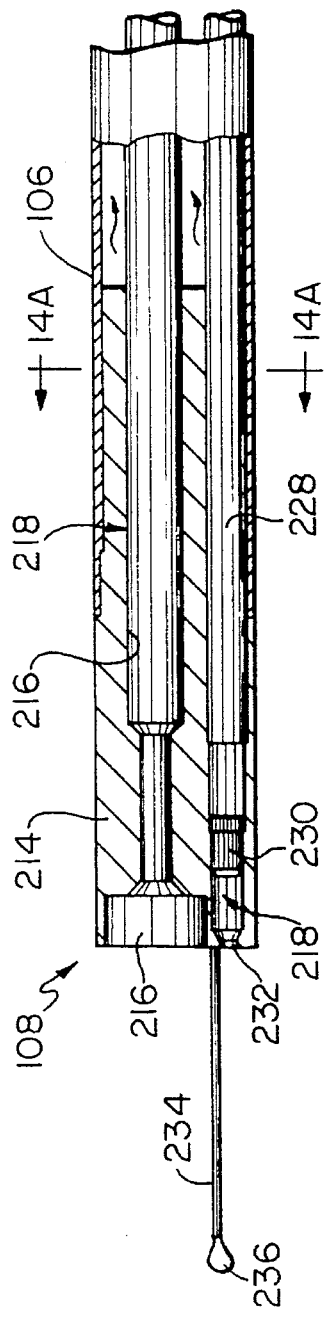
FIG. 15 is a sectional illustration of the distal tip of the device as seen along the line 15—15 of FIG. 14.

FIGS. 14 and 15 illustrate, in enlarged detail, the construction at the tip 108 of the shaft. The device may include a cylindrical tip member 214 that is secured to the distal end of the tubular shaft 106. The tip member 214 includes a plurality of lumens, including a lumen 216 to receive the distal end of the optical fiber 218, a lumen 220 to receive The distal end of the liquid feed tube 120 and a pair of aspiration lumens 222 that communicate with the interior lumen 224 of the shaft 106. The optical fiber lumen 216 may be provided with a reduced diameter distal portion to receive the distal end of the fiber that has been stripped of its cladding. An optically transparent window 226 preferably is mounted to the distal end of tip member 214 to protect the end of the fiber. The window may, if desired, be provided with beam shaping characteristics. The distal end of the liquid feed lumen 220 defines a nozzle 228 that includes a swirl element 230 and tip shape to effect the desired spray pattern.

It is desirable that means be provided to prevent prepolymer liquid from dripping from the distal tip 108 of the device. To that end, the lumen 224 of the shaft 106 is connected to a source of suction to cause aspiration through the distal outlets of the aspiration lumens 222. The aspiration lumens maybe disposed on opposite sides of the liquid emission orifice and will tend to aspirate immediately any liquid that might tend to drip from the outlet orifice 232. The lumen of the shaft may be connected to a source of suction by a tube, illustrated diagrammatically at 223 that is in communication with the shaft lumen and extends out of the housing through aperture 118. The proximal end of the tube may be provided with a-suitable fitting for connection to a source of suction. The suction may be applied at all times during operation of the device.

In order to facilitate orientation and spacing of the distal tip 108 of the device from the tissue to be treated, the device may be provided with a gauging means by which the orientation and spacing of the distal tip with respect to the target tissue may be visually-assessed by the physician. As shown in FIGS. 8, 14 and 15, the device may include a pair of feeler elements 234 attached to and extending distally from the distal end of the tip member 214. The feeler elements 234 diverge and preferably are provided with enlarged bumper pads 236 at their distal ends. The feeler elements 234 extend a distance from the outlet orifice 232 corresponding to the optimal distance of the device from the surface to be sprayed and irradiated. The feeler elements 234 are flexible. They may be formed, for example, from polyethylene. The bumper pads 236 serve to protect the tissue by providing a relatively broad area of contact with the tissue. When the device is in place in the operative region, the physician will be observing the distal end of the device, for example, through a laparoscope. The physician will be able to observe when the bumper pads 236 have engaged the tissue by observing flexing of the feeler elements 234 which will begin to spread apart. Such spreading can be observed and provides an indication that contact has been made. By observing the manner and location of the pads 236 engage the tissue, the physician can verify the orientation and spacing of the tip 108 with respect to the tissue. The gauge also may be made with a single feeler element mounted to the shaft 106 so that it extends at an angle to the axis of the shaft. In this embodiment, the physician can observe the relative movement of the single feeler element with respect to the distal tip of the shaft.

The angle defined between the feelers 234 should be selected to assure sufficient separation so as not to interfere with the spray pattern of liquid prepolymer emitted from the nozzle. The feelers 234 should be spread to be wider than the cone angle 238 defined by the spray 240.

In order to insert the device with the feelers 234 through the trocar cannula 81 (see FIG. 5) leading to the surgical site, the feelers must be drawn together to fit through the trocar cannula. To that end, the device may be provided with a sheath 242, slidable along the shaft 106 and adapted to project distally beyond the tip 108 to enclose and draw together the feelers 234. The slidable sheath 242 can be inserted through the trocar cannula and is provided with an enlarged proximal collar 244 that is too large to be inserted into the trocar cannula 81. The sheath may be shorter than the trocar cannula. When the device is inserted through the trocar cannula, the sheath will maintain the feelers together until the proximal collar engages the proximal end of the trocar cannula. Further advancement of the device will cause the feelers to emerge from the distal end of the sheath and trocar cannula where they will spread under the influence of their own resilience.

Although, for convenience in the foregoing description, certain features of the invention may have been disclosed only in connection with one of the embodiments, it is intended that the characteristics and features of each embodiment may be incorporated in the other, to the extent that they are compatible. For example, feeler gauges or aspiration lumens may be provided with the embodiment illustrated in FIGS. 1–5.

It should be understood that although the invention has been described as being used with a device having a rigid shaft, the invention also may be employed with application systems in which the shaft, or part of the shaft, is flexible or articulated, as in a flexible or articulated catheter. Additionally, it should be appreciated that the invention may be practiced with other compositions than those described explicitly in the above-identified Hubbell patent applications including, but not limited to, compositions that may be later developed.

It also should be understood that the foregoing description of the invention is intended merely to be illustrative thereof and that other embodiments, modifications and equivalents may be apparent to those skilled in the art without departing from its spirit.

Having thus described the invention, what we desire to claim and secure by Letters Patent is:

1. A method of applying polymeric, non-fluent material to mammalian tissue, comprising:

applying an initially entirely fluent, pre-polymeric material to the tissue by emitting the pre-polymeric material from an emission element located on an applicator; and applying to the material actinic light from an emitter of actinic light located on the applicator for a period of time sufficient to convert the material to a polymeric, non-fluent condition.

2. A method as in claim 1, the applying step comprising applying a predetermined volume of fluent, pre-polymeric material to the tissue.

3. A method as in claim 1, wherein the step of applying fluent pre-polymeric material to the tissue involves forming a coating of fluent pre-polymeric material on the tissue, and the step of applying actinic light involves converting the coating of fluent pre-polymeric material to a coating of polymeric, non-fluent material on the tissue.

4. A method as in claim 1, wherein the step of applying pre-polymeric material to the tissue involves emitting the pre-polymeric material from an emission element located at a distal portion of an applicator having a proximal portion and a distal portion, and the step of applying actinic light involves applying the actinic light from an emitter of actinic light located at the distal portion of the applicator.

5. A method as in claim 4 wherein the step of applying actinic light further involves activating a source of actinic light that is connected, via an optical connector, to the emitter of actinic light.

6. A method as in claim 4 wherein the step of applying pre-polymeric material further involves dispersing the pre-polymeric material from a nozzle that is a component of the emission element, in a predetermined pattern.

7. A method as in claim 4, wherein the actinic light is emitted from the distal portion of the applicator in the same direction in which the pre-polymeric material is applied from the distal portion of the applicator.

8. A method as in claim 4, wherein the step of applying actinic light involves applying actinic light to a tissue surface in a pattern at least as large as a dispersion pattern in which the pre-polymeric material is applied to the tissue surface.

9. A method as in claim 4, wherein, following the step of applying pre-polymeric material to the tissue surface in a first pattern, the method involves applying actinic light to the tissue surface in a pattern that is substantially the same shape as that of the first pattern.

10. A method as in claim 4, further comprising allowing a controller that automatically operates the emitter of actinic light to activate the actinic light following the step of applying the pre-polymeric material to the tissue.

11. A method as in claim 1, further comprising inserting the applicator, percutaneously, into the body of a mammal.

12. A method as in claim 1, further comprising inserting the applicator via an incision into a mammal.

13. A method as in claim 1, further comprising inserting the applicator via a natural orifice into a mammal.

14. A method as in claim 4 wherein the distal portion of the applicator is adapted for insertion into a patient and proximal portion remains outside of the patient, the method further comprising inserting the distal portion of the applicator, percutaneously, into the body of a mammal.

15. A method as in claim 4, wherein the distal portion of the applicator is adapted for insertion into a patient and proximal portion remains outside of the patient, the method further comprising inserting the applicator via an incision into a mammal.

16. A method as in claim 14, wherein the distal portion of the applicator is adapted for insertion into a patient and proximal portion remains outside of the patient, the method further comprising inserting the applicator via a natural orifice into a mammal.

17. A method as in claim 2, wherein the step of applying a predetermined volume of fluent, pre-polymeric material to the tissue defines a first cycle of a cyclical procedure, the method further comprising applying a second predetermined volume of fluent pre-polymeric material to the tissue in a second cycle.

18. A method as in claim 17, wherein the first and second predetermined volumes of fluent pre-polymeric material are essentially the same.

19. A method as in claim 17, wherein the step of applying actinic light to the material is effected between the first and second cycles.

20. A method as in claim 1, wherein the step of applying the fluent pre-polymeric material involves spraying the fluent pre-polymeric material onto the tissue.

21. A method of aiming a fluent delivery device and for irradiating fluent material delivered by the device, comprising:

providing a delivery and activating device having an applicator constructed and arranged to deliver fluent material in a predetermined pattern, the device having an emitter that emits electromagnetic radiation in a substantially corresponding pattern;

preliminary irradiating a tissue surface with light in the predetermined pattern using the light pattern as a guide to orient the device at a selected location with respect to the tissue;

thereafter delivering the fluent material onto the tissue at the location in the predetermined pattern; and thereafter emitting electromagnetic radiation from the emitter onto the fluent material to activate the material to convert it to a non-fluent state.

22. A method as in claim 21, wherein the step of delivering the fluent material onto the tissue involves spraying the fluent material onto the tissue.

23. A method as in claim 22, wherein the step of spraying the fluent material onto the tissue involves delivering a bolus of pre-polymer fluid into a gas stream moving at a velocity sufficient to atomize the pre-polymer fluid to form a spray.

24. A method as in claim 22, wherein the spraying step involves spraying the fluent material onto the tissue in a generally conical spray pattern.

25. A method as in claim 21, wherein the step of emitting electromagnetic radiation onto the fluent material to activate the material involves emitting actinic light from the emitter onto the fluent material.

26. A method as in claim 21, wherein the step of delivering fluent material onto the tissue involves delivering a predetermined volume of the fluent material onto the tissue.

27. A method as in claim 21, wherein the steps of delivering the fluent material onto the tissue and thereafter emitting electromagnetic radiation onto the fluent material to convert it to a non-fluent state defines a first cycle of operation, the method further comprising a second cycle involving delivering fluent material onto the tissue and emitting electromagnetic radiation from the emitter onto the fluent material to convert it to a non-fluent state.

28. A method as in claim 27, wherein each of the first and second cycles involves delivering a predetermined volume of fluent material onto the tissue.

29. A method as in claim 28 wherein the predetermined volume of fluent material delivered in each of the first and second cycles is essentially the same.

30. A method as in claim 21, further comprising orienting the delivery and activating device with respect to the tissue with a gauge.

31. A method as in claim 21, further comprising allowing a microprocessor to activate the emitter automatically following the delivery of the fluent material onto the tissue.

32. A method of applying, to mammalian tissue, a polymeric, non-fluent material, comprising:

applying an initially entirely fluent, pre-polymeric material to the tissue by emitting the pre-polymeric material from an emission element located on an applicator; and applying to the material actinic light from an emitter of actinic light located on the applicator for a period of time sufficient to convert the material to a polymeric, non-fluent condition.

33. A method of applying a polymeric, non-fluent material to a surface of tissue internally of a mammal, comprising:

applying percutaneously an initially entirely fluent, pre-polymeric material to a tissue surface internally of a mammal, the material being activatable to a non-fluent, polymeric condition by exposure to actinic light; and thereafter applying to the material actinic light for a sufficient length of time to effect in situ conversion of the material from a pre-polymeric, fluent to a polymeric, non-fluent condition.

\* \* \* \* \*